United States Patent [19]

Capuzzi et al.

[11] Patent Number: 4,902,697

[45] Date of Patent: Feb. 20, 1990

[54] DERIVATIVES OF 2,2-DIMETHYL-CYCLOPROPANECARBOXYLIC ACID

[75] Inventors: Luigi Capuzzi; Franco Bettarini, both of Novara; Paolo Castoro, Vercelli; Pietro Massardo, Milan; Vincenzo Caprioli, S. Martino Siccomario, all of Italy

[73] Assignee: Montedison S.p.A., Milan, Italy

[21] Appl. No.: 89,303

[22] Filed: Aug. 25, 1987

[30] Foreign Application Priority Data

Aug. 27, 1986 [IT] Italy ............................... 21532 A/86
Dec. 23, 1986 [IT] Italy ............................... 22829 A/86

[51] Int. Cl.$^4$ ..................... C07D 213/64; C07C 69/74
[52] U.S. Cl. .................................... 514/351; 514/521; 514/531; 514/346; 514/357; 546/300; 558/407; 560/124
[58] Field of Search ............ 558/407; 560/124; 514/346, 357, 351, 521, 531; 546/300

[56] References Cited

U.S. PATENT DOCUMENTS

| 4,252,820 | 2/1981 | Lantzsch et al. | 514/521 |
| 4,276,306 | 6/1981 | Fuchs et al. | 558/407 |
| 4,285,969 | 8/1981 | Galli et al. | 558/407 |
| 4,297,366 | 10/1981 | Fuchs et al. | 558/407 |
| 4,482,570 | 11/1984 | Piccardi et al. | 558/407 |
| 4,582,856 | 4/1986 | Lantzsch et al. | 558/407 |
| 4,602,038 | 7/1986 | Tessier et al. | 558/407 |

Primary Examiner—William R. Dixon, Jr.
Assistant Examiner—Jerry D. Johnson
Attorney, Agent, or Firm—Stevens, Davis, Miller & Mosher

[57] ABSTRACT

Derivatives of 2,2-dimethylcyclopropanecarboxylic acid endowed with insecticidal and acaricidal activity, and having the formula

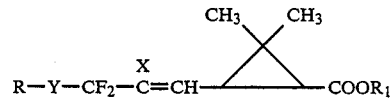

wherein:
R is an alkyl, cycloalkyl, alkenyl or alkynyl radical having from 1 to 8 carbon atoms, optionally substituted with halogen atoms, or R is an aryl radical optionally substituted with halogen atoms, alkyl or alkoxyl radicals;
Y is O or S;
X is H, F, Cl, Br, —$CH_3$, or —$CF_3$;
$R_1$ represents a group having the formula:

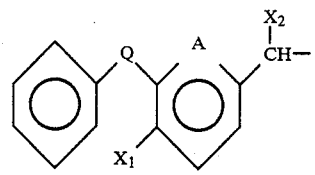

wherein: $X_1$=H or F; $X_2$=H, —CN, or —C≡CH; Q=O or $CH_2$; A=CH or N when $X_1$=H, $X_2$=CN and Q=O.

10 Claims, No Drawings

DERIVATIVES OF 2,2-DIMETHYL-CYCLOPROPANECARBOXYLIC ACID

DECRIPTION OF THE INVENTION

The present invention relates to new compounds having insecticidal and acaricidal activity, which compounds are derivatives of 2,2-dimethyl-cyclopropanecarboxylic acid. Furthermore, the invention relates to processes for preparing such compounds.

Several compounds are known, belonging to the class of synthetic pyrethroids, which are used for fighting noxious insects both in the agrarian and in the domestic field; among these the most important compounds are derivatives of 2,2-dimethylcyclopropanecarboxylic acid such as for instance, permetrina, cypermetrina and deltametrina ("Synthetic Pyrethroids", A.C.S. Symposium Series 42, 1977).

These and other synthetic pyrethroids show, however, an important limitation concerning low activity against acari.

Applicants have now found some pyrethroids which, besides having a high insecticidal activity, have a good acaricidal activity as well.

Therefore, an object of the present invention is to provide derivatives of 2,2-dimethyl-cyclopropane carboxylic acid having the formula:

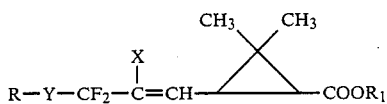

wherein:
R represents an alkyl, cycloalkyl, alkenyl or alkynyl group containing from 1 to 8 carbon atoms, optionally substituted with halogen atoms, or R represents an aryl group, optionally substituted with halogen atoms, alkyl or alkoxyl radicals;
Y represents O or S;
X represents H, F, Cl, Br, —CH$_3$ or —CF$_3$;
R$_1$ represents a group having the formula:

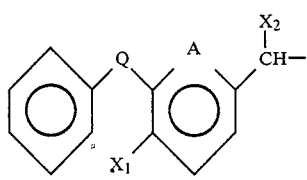

wherein X$_1$ is H or F; X$_2$ is H, —CN or —C≡CH; Q is O or CH$_2$; A is CH or N when X$_1$ is H, X$_2$ is CN and Q is O.

Such products show, besides a high activity against noxious insects both in agrarian and in domestic fields (Hemiptera, Lepidoptera, Coleoptera, Diptera and Blaptoidea), also a good acaricidal activity, higher than that of the known pyrethroids.

The preparation of the compounds of formula (I) is carried out by esterification of a carboxylic acid or of an acylic derivative thereof having the formula (II):

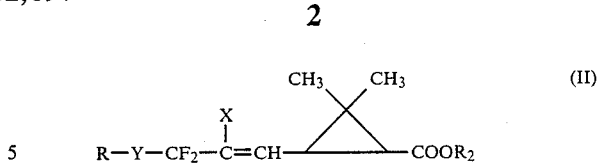

wherein R, Y, X have the meanings as specified hereinbefore, and R$_2$ represents H, Cl or an alkyl radical containing from 1 to 4 carbon atoms, with an alcohol of formula R$_1$—OH, wherein R$_1$ has the same meaning as in formula (I).

The esterification reaction may be carried out according to different techniques which are usually used in organic chemistry.

Preferably, an acid having formula (II) (R$_2$=H) is converted into acyl chloride by means of a suitable agent such as for instance oxalyl chloride, thionyl chloride, phosphorus pentachloride and the like, in an inert solvent at a temperature ranging between room temperature and reflux temperature, and it is then reacted with an equivalent of alcohol of formula R$_1$—OH in an inert anhydrous organic solvent at room temperature in the presence of an organic base preferably consisting of a tertiary amine such as pyridine and triethylamine.

The alcohols having formula R$_1$—OH are known compounds, which are generally used for the synthesis of synthetic pyrethroids.

The compounds having the formula (II) are new, and, as such, they form another object of the present invention.

The compounds having the formula (II), when R$_2$ is a hydrogen atom or a C$_1$-C$_4$ alkyl radical, may be prepared by a process, and this forms a further object of the present invention, consisting or consisting essentially in reacting a metal salt having the formula RY$^-$-M$^+$ (V) with a difluoroolefin having the formula:

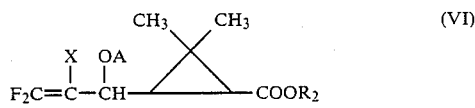

in the presence of an organic solvent at a temperature ranging from −78° C. to the boiling temperature of the solvent, according to the following reaction scheme:

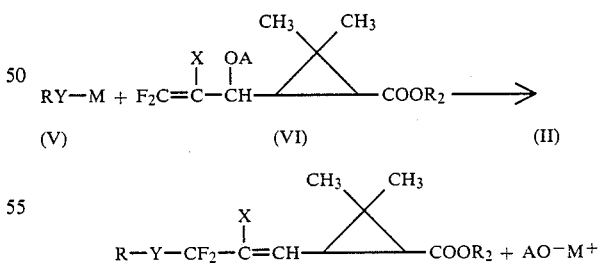

wherein R, Y, X have the meanings as defined hereinbefore, R$_2$ is H or a C$_1$-C$_4$ alkyl radical, M is an alkali metal selected from the group consisting of K, Na and Li, A represents H or an acylic or sulfonic group, selected preferably from the group consisting of CH$_3$CO, CH$_3$SO$_2$, CF$_3$SO$_2$, CH$_3$—C$_6$H$_5$—SO$_2$.

The following solvents are suitable for use in the reaction: linear or cyclic ethers such as diethylether, tetrahydrofuran, dioxane, diglyme; aprotic dipolar solvents such as N,N-dimethylformamide, dimethylsulfoxide, sulfolane, hexamethylphosphorotriamide; nitrogenated heterocyclic solvents such as pyridine, picoline; optionally use may be made, as solvent, of the protic RYH compound corresponding to the metal salt (II) employed in the reaction.

Such solvents are used alone or in admixture; preferably use is made of the following solvents: tetrahydrofuran, dimethylformamide, dioxane, hexamethylphosphorotriamide and pyridine.

The preferred reaction temperature ranges between −30° and 25° C.

The reactants are used in substantially stoichiometric ratios.

The compounds having the formula (VI):

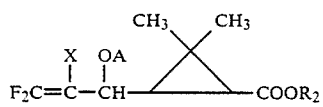

are known products or they may be readily obtained by processes described in the literature, such as for instance Tetrahedron Letters, 27, 3655 (1986).

The procedure may vary widely according to the compounds employed and does not represent any critical factor.

A preferred embodiment for carrying out the process consists or consists essentially in adding the compound of formula (VI), dissolved in the selected solvent, to a suspension of metal salt RYM in the reaction solvent. According to an alternative embodiment, metal salt RYM may be added, in the solid form or in suspension, to a solution of the comnpound of formula (VI).

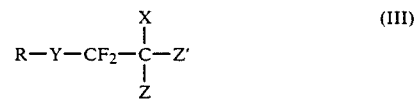

wherein R, X and Y have the same meanings as recorded above for the formula (I), whereas Z and Z' are halogen atoms, which may be the same or different. Preferably when X=H, —CH₃ or —CF₃', Z and Z' represent Cl, Br or I; when X=F, Z=Z'=Br or Cl, or Z=F and Z'=I; when X=Cl, Z and Z' may be Br or Cl; when X=Br, Z=Z'=Br.

The compounds having formula (III) are known products or may readily be obtained by processes disclosed in the literature such as, for instance, in Angew. Chem., Int. Ed. Engl., 24 (1985) 871, in U.S. Pat. No. 3,388,078 (C.A. 69: 28654a), and in J. Org. Chem. 50 (1985), 4047–4051.

Compounds having the formula (II) may be prepared preferably according to one of the methods described hereinafter.

METHOD A

According to a process similar to that disclosed in DOS 2539895 (1976) and in Bull. Chem. Soc. Jpn., 52, 1511 (1979), a compound of formula (III) is added to the ethyl ester of 3,3-dimethyl-pentenoic acid in the presence of a suitable promoter of free radical reactions (step 1A); the thus-obtained adduct is cyclicized and (step 2A) further dehydrohgalogenated (step 3A) by treatment with a base to yield a compound having the formula (II) with $R_2 = C_2H_5$:

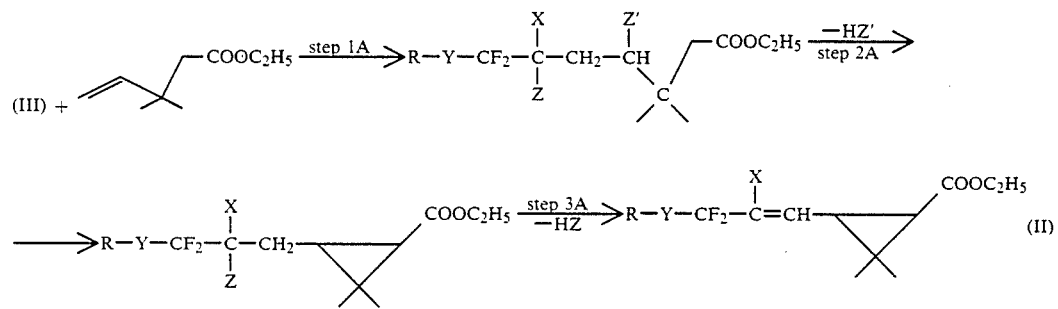

Moreover, compounds having the formula (II) may be prepared by modifying a few of the usual synthetic methods of pyrethroid chemistry, starting from poly fluorohalogenated ethers having the formula (III):

METHOD B

By operating as disclosed in European patent application No. 187,674, a compound of formula (III) is reacted with caronaldehyde (ethyl-2,2-dimethyl-3-formyl-cyclopropane-carboxylate) in the presence of metals such as zinc or magnesium (step 1B); by subsequent dehydroxyhalogenation of carbinol of formula (IV), for instance by acetylation, and subsequent treatment with Zn (step 2B), a compound of the formula (II) is obtained wherein $R_2 = C_2H_5$.

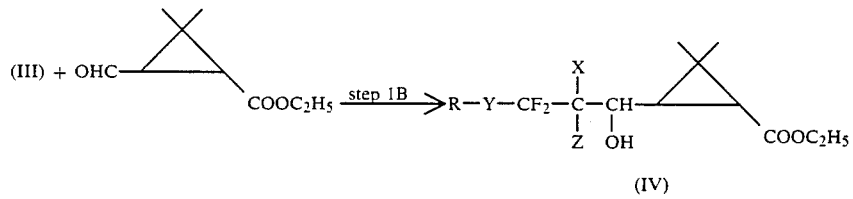

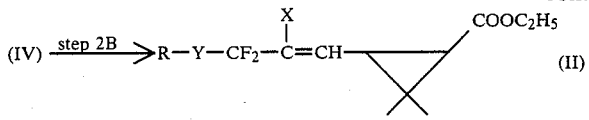

METHOD C

By operating as disclosed, for instance, in J.A.C.S., 101,5853 (1979), a compound of formula (III) is added to acrylic acid in the presence of promoters of free radical reactions (step 1C); the obtained adduct is converted into acyl chloride (step 2C) that is then reacted with triethylamine and isobutylene (step 3C); the obtained intermediate is isomerized by means of catalytic amounts of triethylamine (step 4C) to yield a 4-halocyclobutanone, that undergoes easily a Favorskii rearrangement by treatment with a base at room temperature (step 5C). A further basic treatment yields a compound having formula (II) with $R_2=H$ (step 6C).

Aphides and the like, and furthermore in having a satisfactory acaricidal activity.

On account of their positive characteristics, the compounds of formula (I) may be used in protecting cultivations of agrarian interest as well as in protecting from noxious insects environments frequented by men, domestic animals and breeding cattle.

For practical purposes, both in agriculture and in other fields, the compounds of the invention may be usefully employed in the form of suitable compositions.

These compositions contain, besides one or more components of formula (I) as active principle, inert solid carriers (for instance kaolin, silica, talc, attapulgite, diatomaceous earth and the like) or liquid carriers (or-

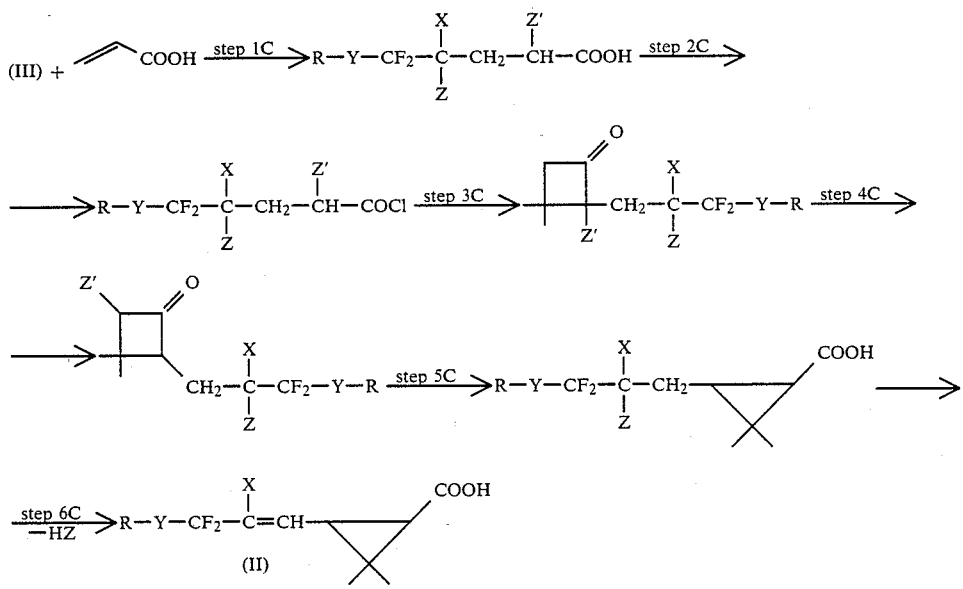

The application of methods A and C generally leads to compounds of formula (II) having prevailingly cis configuration with respect to cyclopropane whereas, by applying method B to a mixture of caronaldehyde in 1/1 cis/trans isomeric ratio, the trans-isomers are prevailingly obtained.

The compounds having general formula (I) may be in the form of mixtures of isomers.

The separation of the mixtures into their components may be carried out according to well known chemical techniques, such as column chromatography or thin layer chromatography.

The isolation and use of any steric and/or configuration isomer, as well as the direct use of the mixtures that may be obtained by preparing the compounds as well as the use of the mixtures coming from an incomplete separation of the isomers all fall within the spirit and scope of the present invention.

As above mentioned, the compounds having formula (I) are endowed with a high insecticidal activity.

Their characterization consists in having a wide action spectrum against insects belonging to different families such as Lepidoptera, Diptera, Coleoptera, ganic solvents, vegetable or mineral oils, water and mixtures thereof) and optionally other additives of common use in the formulation field such as surfactants, suspending agents, dispersing agents, and wetting agents.

For particular application needs or in order to widen the action spectrum of the compositions, other active ingredients, such as for instance other insecticides or acaricides, herbicides, fungicides or fertilizers, may be added to the compositions described herein.

The application doses vary as a function of different factors, such as the kind and degree of infestation, the kind of composition that has been used, climatic and environmental factors.

For practical uses in agriculture, doses of a compound of formula (I) ranging from 10 to 500 g/ha give satisfactory results.

The following examples will be given in order still better to illustrate the invention.

EXAMPLE 1

Synthesis of trans- α-cyano-m-phenoxybenzyl 2,2-dimethyl-3-(2-chloro-2-methoxydifluoromethyl)vinyl-cyclopropanecarboxylate (Compound No. 1).

1.5 g of trans-2,2-dimethyl-3-(2-chloro-2-methoxydifluoromethyl)vinyl-cyclopropanecarboxylic acid, whose preparation will be described in Example 6 below, were dissolved in 15 ml of benzene. 3.5 g of oxalyl chloride were added dropwise to the solution. The whole was kept under stirring at room temperature over 3 hours in an inert atmosphere and then the solvent was evaporated at reduced pressure; the residue, after having been treated with anhydrous ether, was dripped into a solution of 2.25 g of α-cyano-m-phenoxybenzylalcohol in 3 cc. of pyridine and 20 cc. of anhydrous ether.

The whole was kept under stirring overnight, the precipitate was filtered, and the filtrate after having been washed with HCl at 1%, with sodium bicarbonate, and with brine, was dehydrated and dried.

A raw oil (3.5 g) was obtained that was analyzed by silica gel chromatography to yield 2.1 g of pure product.

N.M.R. (CDCl$_3$) δ=1.15–1.3 (m. 6H); 1.75 (d. 1H); 2.3–2.55 (dd. 1H); 3.6 (s. 3H); 6.05 (d. 1H); 6.35 (d. 1H); 6.85–7.5 (m. 9H).

Mass: 461 (M+, 0.1%), 209 (100%), 208, 181, 81 (CF$_2$OCH$_3$).

EXAMPLE 2

Synthesis of cis-α-cyano-m-phenoxybenzyl 2,2-dimethyl-3-(2-chlorophenoxydifluoromethyl)vinyl-cyclopropanecarboxylate (Compound No. 2)

1.5 g of cis-2,2-dimethyl-3-(2-chloro-2-p-chlorophenoxydifluoromethyl)vinyl-cyclopropanecarboxylic acid, whose preparation will be described in Example 7 below, were dissolved in 15 cc. of benzene. 2.5 cc. of oxalyl chloride were added. The whole was kept under stirring at room temperature over 3 hours and then the solvent was evaporated in a rotavapor apparatus; the residue, after having been treated with anhydrous ether, was dripped into a solution of 2 g of α-cyano-m-phenoxy-benzylalcohol in 3 cc of pyridine and 20 cc of anhydrous ether. The whole was kept under stirring overnight, the precipitate was filtered and the filtrate, after having been washed with HCl at 1%, with sodium bicarbonate, and with brine, was dehydrated and dried. A raw oil (3 g) was obtained that was analyzed by silica gel chromnatography to yield 1.9 g of pure product.

N.M.R. (CDCl$_3$) δ:1.25 (bs. 6H); 1.6–2.35 (m. 2H); 6.2 (d. 1H); 7.5–6.6 (m. 14H).

EXAMPLE 3

Synthesis of trans-α-cyano-m-phenoxybenzyl 2,2-dimethyl-3-(2-chloro-2-p-chlorophenoxydifluoromethyl) vinyl-cyclopropanecarboxylate (Compound No. 3)

1.8 g of trans-2,2-dimethyl-3-(2-chloro-2-p-chlorophenoxydifluoromethyl) vinyl-cyclopropanecarboxylic acid, whose preparation will be described in Example 8 below, were dissolved in 15 cc of benzene. 2.5 cc of oxalyl chloride were added. The whole was kept under stirring at room temperature over 3 hours and then the solvent was evaporated in a rotavapor apparatus; the residue, after having been treated with anhydrous ether, was dripped into a solution of 2 g of α-cyano-m-phenoxy-benzylalcohol in 3 cc of pyridine and 20 cc of anhydrous ether.

The whole was kept under stirring overnight, the precipitate was filtered and the filtrate, after having been washed with HCl at 1%, with sodium bicarbonate, and with brine, was dehydrated and dried. A raw oil (3 g) was obtained that was analyzed by silica gel chromatography to yield 1.9 g of pure product.

N.M.R. (CDCl$_3$) δ:1.32–1.13 (m. 6H); 1.7 (d. 1H); 2.4 (dd 1H); 6.0 (d. 1H); 6.18 (d. 1H); 7.5–6.6 (m. 13H).

EXAMPLE 4

Synthesis of cis-α-cyano-m-phenoxybenzyl 2,2-dimethyl-3-(2-chloro-p-ethoxyphenoxydifluoromethyl) vinyl-cyclopropanecarboxylate (Compound No. 4)

1.5 g of cis-2,2-dimethyl-3-(2-chloro-2-p-ethoxyphenoxydifluoromethyl vinyl-cyclopropanecarboxylic acid, that will be described in Example 9 below, were dissolved in 15 ml of benzene, then 3.5 g of thionyl chloride were added. The whole was kept under stirring at 80° C. over 2 hours and then evaporated at reduced pressure; the residue, after having been treated with anhydrous ether, was dripped into a solution of 2.25 g of m-phenoxybenzaldehyde-cyanohydrin in 3 cc. of triethylamine and 20 cc of anhydrous ether.

The whole was kept under stirring overnight, the precipitate was filtered and the filtrate, after having been washed with HCl at 1%, with sodium bicarbonate, and with brine, was dehydrated and dried. A raw oil (3.2 g) was obtained that was analyzed by silica gel chromatography to yield 2 g of pure product.

N.M.R. (CDCl$_3$) δ:1.1–1.4 (m. 9H); 2.3–1.8 (m. 2H); 3.86 (q. 2H); 6.15 (d. 1H); 7.5–6.6 (m. 14H).

EXAMPLE 5

By following procedures similar to those disclosed in the preceding examples, the following compounds, as isomeric mixtures, were prepared, starting from 2,2-dimethyl-3-(2-bromo-2-methoxydifluoromethyl)-ethenyl-cyclopropanecarboxylic acid:

α-cyano-3-phenoxybenzyl 2,2-dimethyl-3-(2-bromo-2-methoxydifluoromethyl)-ethenyl-cyclopropanecarboxylate (Compound No. 5); and, starting from 2,2-dimethyl-3-(2-chloro-2-ethylthiodifluoromethyl)-ethenyl-cyclopropanecarboxylic acid:

α-cyano-3-phenoxybenzyl 2,2-dimethyl-3-(2-chloro-2-ethylthiodifluoromethyl)-ethenyl-cyclopropanecarboxlate (Compound No. 6).

3-phenoxybenzyl 2,2-dimethyl-3-(2-chloro-2-ethylthiodifluoromethyl)-ethenyl-cyclopropancarboxylate (Compound No. 7); and, starting from 2,2-dimethyl-3-(2-chloro-2-(2,2,2-trifluoroethoxy)-difluoromethyl)-ethenyl-cyclopropanecarboxylic acid:

3-phenoxybenzyl 2,2-dimethyl-3-(2-chloro-2-(2,2,2-trifluoroethoxy)-difluoromethyl)-ethenyl-cyclopropanecarboxylate (Compound 8)

α-cyano-3-phenoxybenzyl 2,2-dimethyl-3-(2-chloro-(2,2,2-trifluoroethoxy)-difluoromethyl)-ethenyl-cyclopropanecarboxylate (Compound No. 9);

3-phenoxy-4-fluorobenzyl 2,2-dimethyl-3-(2-chloro-2-(2,2,2-trifluoroethoxy)-difluoromethyl)-ethenyl-cyclopropanecarboxylate (Compound No. 10);

α-cyano-3-phenoxy-4-fluorobenzyl 2,2-dimethyl-3-(2-chloro-2-(2,2,2-trifluoroethoxy)-difluoromethyl)-ethenyl-cyclopropanecarboxylate (Compound No. 11);

3-benzyl-benzyl 2,2-dimethyl-3-(2-chloro-2-(2,2,2-trifluoroethoxy)-difluoromethyl)-ethenyl-cyclopropanecarboxylate (Compound No. 12);

α-cyano-3-(2-pyridyloxy)-benzyl 2,2-dimethyl-3-(2-chloro-2-(2,2,2-trifluoroethoxy)-difluoromethyl)-ethenyl-cyclopropanecarboxylate (Compound No. 13); and, starting from 2,2-dimethyl-3-(2-fluoro-2-(2,2,2-trifluoroethoxy)-difluoromethyl)-ethenyl-cyclopropanecarboxylic acid:

α-cyano-3-phenoxybenzyl 2,2-dimethyl-3-(2-fluoro-2-(2,2,2-trifluoroethoxy)-difluoromethyl)-ethenyl-cyclopropanecarboxylate (Compound No. 14); and, starting from 2,2-dimethyl-3-(2-chloro-2-(2,2,3,3-tetrafluoropropoxy)-difluoromethyl)-ethenyl-cyclopropanecarboxylic acid:

α-cyano-3-phenoxybenzyl 2,2-dimethyl-3-(2-chloro-2-(2,2,3,3-tetrafluoropropoxy)-difluoromethyl)-ethenyl-cyclopropanecarboxylate (Compound No. 15); and, starting from 2,2-dimethyl-3-(2-chloro-2-(2,2,3,3,3-pentafluoropropoxy)-difluoromethyl)-ethenyl-cyclopropanecarboxylic acid:

3-benzyl-benzyl 2,2-dimethyl-3-(2-chloro-2-(2,2,3,3,3-pentafluoropropoxy)-difluoromethyl-ethenyl-cyclopropanecarboxylate (Compound No. 16);

α-cyano-3-(2-pyridyloxy)-benzyl 2,2-dimethyl-3-(2-chloro-2-(2,2,3,3,3-pentafluoropropoxy)-difluoromethyl)-ethenyl-cyclopropanecarboxylate (Compound No. 17);

α-ethenyl-3-phenoxy-benzyl 2,2-dimethyl-3-(2-chloro-2-(2,2,3,3,3-pentafluoropropoxy)-difluoromethyl)-ethenyl-cyclopropanecarboxylate (Compound No. 18);

EXAMPLE 6

Synthesis of trans-2,2-dimethyl-3-(2-chloro-2-methoxy-difluoromethyl)vinyl-cyclopropanecarboxylic acid Step 1B—100 cc of anhydrous DMF, 8.5 g of a 1:1 mixture of cis/trans caronaldehyde (0.05 moles), and 3.5 g of Zn were fed into a 3-neck flask equipped with a cooler and magnetic stirrer, under nitrogen. Then 12 g of $CH_3OCF_2CCl_3$ were dripped under stirring into the mixture. The mixture was kept at 40° C. over two hours and then cooled to room temperature and the reaction was stopped by means of HCl at 10%. Upon extraction with ether (3×100 cc), the extract was washed with a solution saturated with sodium bicarbonate and with water and salt, dehydrated and dried.

Thus obtained were 14 g of a yellow oil containing ethyl 2,2-dimethyl-3-(1-hydroxy-2,2-dichloro-3,3-difluoro-3-methoxy) propyl-cyclopropanecarboxylate that was used without any further purification.

Step 2B—14 g of raw product obtained by step 1B were dissolved in 30 cc of anhydrous DMF and 10 cc of pyridine. 10 cc of acetic anhydride were dripped into the mixture that was then brought to 60° C. over 3 hours. The carbynol conversion was checked by a monitor through G.L.C. When the conversion was over, 8 cc of glacial acetic acid and 4 g of Zn were added to the mixture, which was then kept at 60° C. over a further 2 hours. At the end of that time the mixture was cooled, diluted with water and extracted several times by means of ether; the ethereal extracts were collected, washed with sodium bicarbonate and saturated brine, dehydrated and dried. 6 g of a raw product were obtained that was analyzed by silica gel chromatograph (hexane/ether 9/1) to yield 3.9 g of trans-ethyl 2,2-dimethyl-3-(2-chloro-2-methoxy difluoromethyl)vinyl-cyclopropanecarboxylate.

N.M.R.: $(CDCl_3)$ δ:1.1–1.4 (m.9H); 1.8 (d. 1H); 2.4 (dd. 1H); 3.6 (s. 3H); 3.9 (q. 2H); 6.05 (d. 1H).

Hydrolysis 3.9 g of the product coming from step 2B were dissolved in 30 cc. of ethanol at 95% containing 1.68 g of KOH.

The resulting solution was kept under stirring at 60 degrees over 2 hours.

The mixture was evaporated at reduced pressure, treated with ether, and washed with soda at 10%. Then the aqueous extract was washed with ether again and successively acidified with HCl at 10%.

The acid solution was extracted with ether several times, the extracts were collected, washed with saturated brine, dehydrated with sodium, and dried in the rotavapor apparatus.

3.3 g of product were obtained.

N.M.R.: $(CDCl_3)$ δ: 1.2–1.35 (s. 6H); 1.8 (d. 1H); 2.4 (dd. 1H); 3.6 (s. 3H); 6.03 (d. 1H); 9.7 (bs. 1H).

EXAMPLE 7

Synthesis of cis-2,2-dimethyl-3-(2-chloro-2-p-chlorophenoxydifluoromethyl)vinyl-cyclopropane carboxylic acid Step 1A—7.4 g of 1-p-chlorophenoxy)-1,1-difluoro-2,2,2-trichloroethane, 3.9 g of ethyl 3,3-dimethylpentenoate, 30 cc of $CH_3CN$, 1 g of CuCl, and 1.5 g of dipyridyl were fed into a three-neck flask under nitrogen.

The whole was kept under magnetic stirring at 80° C. over 4 hours. At the end the mixture was cooled, diluted with ether, the insoluble salts were filtered, washed with diluted HCl and then with sodium bicarbonate and saturated brine, followed by dehydration and drying.

Thus obtained were 10.55 g of an oil containing ethyl 3,3-dimethyl-4,6,6-trichloro-7,7-difluoro-7-(p-chlorophenoxy) heptanoate that was used without any purification at the next step.

Step 2A—The raw product prepared at step 1A was dripped into a solution of 4.1 g of sodium ethylate in 125 cc of anhydrous ethanol.

The mixture was stirred over two hours at room temperature, after which the solvent was evaporated at reduced pressure; acidified with HCl at 5% and extracted with ether several times; the organic extracts, after having been collected, were washed with sodium bicarbonate and with water and salt, dehydrated, dried and analyzed by silica gel chromatography to yield 4.2 g of ethyl 2,2-dimethyl-3-(2,2-dichloro-3,3-difluoro 3-p-chlorophenoxy)propylcyclopropanecarboxylate.

N.M.R. $(CDCl_3)$ δ:1.1–1.35 (m. 9H); 1.65–2.2 (m. 2H); 3.15–3.3 (m. 2H); 4.02 (q. 2H); 7.0–7.4 (m. 4H).

Step 3A—The product obtained at step 2A was dissolved in 50 cc of anhydrous DMF.

3.2 g of DBU (diazabicycloundecene) were added to the solution and the whole was brought to 100° C. over 4 hours. At the end the solution was cooled, acidified with HCl at 10%, and extracted with ether several times. The ethereal extracts were washed repeatedly with water, then dehydrated, dried and analyzed by silica gel chromatography to yield 2.7 g of cis-ethyl 2,2-dimethyl-3-(2-chloro-2-p-chlorophenoxydifluoromethyl) vinylcyclopropanecarboxylate.

N.M.R. (CDCl$_3$) δ:1.15–1.4 (m. 9H); 1.65–2.4 (m. 2H); 4.05 (q. 2H); 6.8 (d. 1H); 7.0–7.35 (m. 4H).

Hydrolysis 2.7 g of the product obtained by step 3A were dissolved in 30 cc of ethanol at 95% containing 1.38 g of KOH.

The resulting solution was kept under stirring at 60° C. over 2 hours.

The mixture was evaporated at reduced pressure, treated with ether, and washed with soda at 10%. The aqueous extract was washed with ether again and then acidified with HCl at 10%.

The acid solution was extracted with ether several times, the extracts were collected, washed with saturated brine, dehydrated with sodium sulphate, and dried in the rotavapor apparatus.

2.2 g of acid were obtained.

EXAMPLE 8

Synthesis of trans-2,2-dimethyl-3-(2-chloro-2-p-chlorophenoxy-difluoromethyl)vinyl-cyclopropanecarboxylic acid Step 1B—50 cc. of anhydrous DMF, 4.25 g of caronaldehyde (mixture 1:1 cis:trans) (0.025 moles), and 1.75 g of Zn were fed into a 3-neck flask equipped with a cooler and magnetic stirrer, under nitrogen atmosphere.

Then 10 g of 1-(p-chlorophenoxy)-1,1-difluoro-2,2,2-trichloroethane were dripped into the mixture, under stirring.

The mixture was kept at 40° C. over two hours, after which it was cooled to room temperature and the reaction was stopped by means of HCl at 10%.

One extracted with ether (3×70 cc); the extract was washed with a solution saturated with sodium bicarbonate and with water and salt, dehydrated, and dried.

One thus obtained 11 g of a yellow oil containing ethyl 2,2-dimethyl-3-(1-hydroxy-2,2-dichloro-3,3-difluoro-3-p-chlorophenoxy)propylcyclopropanecarboxylate.

Step 2B—11 g of the product coming from step 1B were dissolved in 20 cc of anhydrous DMF and 5 cc of pyridine. 5 cc of acetic anhydride were dripped into the mixture, which was then brought to 60° C. over 3 hours. The carbinol conversion was checked by means of a monitor through G.L.C.

When the conversion was over, 4 cc of glacial acetic acid and 2 g of Zn were added to the mixture that was kept at 60° C. over a further 2 hours.

At the end the mixture was cooled, diluted with water, and extracted with ether several times; the ethereal extracts were collected, washed with sodium bicarbonate and with water and salt, dehydrated and dried.

5 g of raw product were obtained that were analyzed by silica gel chromatography to yield 3.1 g of trans-ethyl-2,2-dimethyl-3-(2-chloro-2-p-chlorophenoxy-difluoromethyl)vinyl-cyclopropanecarboxylate.

N.M.R. (CDCl$_3$) δ:1.0–1.3 (m. 9H); 1.6 (d. 1H); 2.3 (dd. 1H); 4.02 (q. 2H); 6.05 (d. 1H); 7.15 (q. 4H).

Hydrolysis 3.1 g (0.0082 moles) of ester coming from step 2B were dissolved in 30 cc of ethanol at 95% containing 1.05 g of KOH.

The resulting solution was kept under stirring at 60° C. over 2 hours.

The mixture was evaporated at reduced pressure, treated with ether, and washed with soda at 10%. Then the aqueous extract was washed with ether again and acidified with HCl at 10%.

The acid solution was extracted with ether several times, the extracts were collected, washed with saturated brine, dehydrated with sodium sulfate, and dried in the rotavapor apparatus.

2.7 g of acid were obtained.

EXAMPLE 9

Synthesis of cis-2,2-dimethyl-3-(2-chloro-2-p-ethoxy-phenoxy-difluoromethyl)vinyl-cyclopropanecarboxylic acid Step 1A—60 cc of acetonitrile, 6 g (19.6 millimoles) of 1-(p-ethoxyphenoxy)-1,1-difluoro-2,2,2-trichloroethane, 4.6 g (29.5 millimoles) of ethyl 3,3-dimethyl-4-pentenoate, 0.2 g (2 millimoles) of anhydrous CuCl, and 0.3 g (2 millimoles) of dipyridyl were fed, according to the indicated order, into a 3-neck flask, under nitrogen head.

The mixture was kept under magnetic stirring at 80° C. over 4 hours. At the end the mixture was cooled, diluted with water and the insoluble salts were filtered; the filtrate was washed with diluted HCl and then with sodium bicarbonate and with saturated brine, dehydrated and dried.

One thus obtained 9.14 g of an oil containing ethyl 3,3-dimethyl-4,6,6-trichloro-7,7-difluoro-7-p-ethoxy-phenoxy-heptanoate that was used without any purification at the next step.

Step 2A—100 ml of anhydrous ethanol, 3.4 g of sodium ethylate and 9.14 g of the raw product coming from step 1A were fed into a three-neck flask under nitrogen.

The mixture was stirred over two hours at room temperature, after which the solvent was evaporated at reduced pressure; one acidified with HCl at 5% and one extracted with ether several times; the organic extracts, after having been collected, were washed with sodium bicarbonate with water and salt, dehydrated and dried.

One obtained 6.3 g of a raw oil containing ethyl 2,2-dimethyl-3-(2,2-dichloro-3,3-difluoro-3-p-ethoxy-phenoxy)propylcyclopropanecarboxylate that was used without any further treatment in the next step.

Step 3A—The product obtained by step 2A was dissolved in 50 cc of anhydrous D.M.F.

3.2 g of DBU (diazabicycloundecene) were added to the solution and the whole was brought to 100° C. over 4 hours. At the end the solution was cooled, acidified with HCl at 10%, and extracted with ether several times. The ethereal extracts were washed with water repeatedly, then dehydrated, dried and analyzed by silica gel chromatography to yield 1.8 g of cis-ethyl 2,2-dimethyl-3-(2-chloro-2-p-ethoxy-phenoxydi-fluoromethyl)vinylcyclopropanecarboxylate.

N.M.R. (CDCl$_3$) δ: 1.1–1.5 (m. 12H); 1.7–2.4 (m. 2H); 3.7–4.2 (m. 4H); 6.6–7.15 (m. 5H).

Hydrolysis 1.8 g of the product obtained by step 3A were dissolved in 30 cc of ethanol at 95% containing 0.55 g of ground KOH.

The resulting solution was kept under stirring at 60° C. over 2 hours.

The mixture was evaporated at reduced pressure, treated with ether and washed with soda at 10%. Then the aqueous extract was washed with ether again and acidified with HCl at 10%.

The acid solution was extracted with ether several times, the extracts were collected, washed with saturated brine, dehydrated with sodium sulfate and dried in the rotavapor apparatus.

2.2 g of acid were obtained.

EXAMPLE 10

Synthesis of trans-ethyl 2,2-dimethyl-3(2-chloro-2-(2,2,2-trifluoroethoxy)-difluoromethyl)-ethenyl-cyclopropanecarboxylate 20 cc of anhydrous THF and 480 mg of a suspension containing 50% of NaH in vaseline oil (10 mmoles) were loaded into a 3-neck flask equipped with a dropping funnel and magnetic stirrer. 1 g (10 mmoles) of 2,2,2-trifluoroethanol was added cautiously to the suspension, while keeping the temperature at 20° C.

After a few minutes, the solution was limpid, was cooled down to −30° C. and a solution of 3.1 g (10 mmoles) of transethyl 2,2-dimethyl-3-(1-acetoxy-2-chloro-3,3-difluoro)-2-propenyl-cyclopropanecarboxylate was added dropwise to the cooled solution. After 15 minutes at −30° C. the reaction was stopped by means of 30 cc of a saturated solution of $NH_4Cl$; the mixture was extracted with ether, rinsed with a solution saturated with sodium bicarbonate, rinsed with brine, dehydrated and dried. After a quick silica gel chromatography 3 g of product (1) (86%) were obtained.

N.M.R. ($CDCl_3$) δ: 1.2–1.35 (m, 9H); 1.75 (d, 1H); 2.4 (dd, 1H); 4.15 (q, 2H); 4.2 (q, 2H); 6.15 (d, 1H).

EXAMPLE 11

Synthesis of trans-ethyl 2,2-dimethyl-3-(2-chloro-2-(2,2,3,3-tetrafluoropropoxy)-difluoromethyl)-ethenyl-cyclopropanecarboxylate.

20 cc of anhydrous THF and 480 mg of a suspension containing 50% of NaH in vaseline oil (10 mmoles) were loaded into a 3-neck flask equipped with a dropping funnel and magnetic stirrer. 1.32 g (10 mmoles) of 2,2,3,3-tetrafluoropropanol were added cautiously to the suspension, while keeping the temperature at 20° C.

After a few minutes, the solution, when limpid, was cooled down to −30° C. and a solution of 3.1 g (10 mmoles) of trans-ethyl 2,2-dimethyl-3-(1-acetoxy-2-chloro-3,3-difluoro)2-propenylcyclopropanecarboxylate was added dropwise to the cooled solution. After 10 minutes at −30° C. the reaction was stopped by means of 30 cc of a solution saturated with $NH_4Cl$; the mixture was extracted with ether, rinsed with a solution saturated with sodium bicarbonate, rinsed with brine, dehydrated and dried. After a quick silica gel chromatography 3.2 g of product (2) (84%) were obtained.

N.M.R. ($CDCl_3$) δ: 1.2–1.35 (m, 9H); 1.75 (d, 1H); 2.4 (dd, 1H); 4.2 (q, 2H); 4.2 (t, 2H); 5.95 (tt, 1H); 6.15 (d, 1H).

EXAMPLE 12

Synthesis of trans-ethyl 2,2-dimethyl-3-(2-chloro-2-methoxydifluoromethyl)-ethenyl-cyclopropanecarboxylate 20 cc of anhydrous THF and 3.1 g (10 mmoles) of trans-ethyl 2,2-dimethyl-3-(1-acetoxy-2-chloro-3,3-difluoro)2-propenylcyclopropanecarboxylate were loaded into a 3-neck flask equipped with a dropping funnel and magnetic stirrer. The mixture was cooled down to −30° C. and 540 mg (10 mmoles) of $CH_3ONa$ were added gradually in parts. After 30 minutes at −30° C. the reaction was stopped by means of a solution saturated with $NH_4Cl$; the resulting mixture was extracted with ether, rinsed with a solution saturated with sodium bicarbonate and with brine, dehydrated and dried. After silica gel chromatography 2.6 g of product (3) (92%) were obtained.

N.M.R. ($CDCl_3$) δ: 1.1–1.4 (m 9H); 1.8 (d, 1H); 2.4 (dd, 1H); 3.6 (s, 3H); 3.9 (q, 2H); 6.05 (d, 1H).

EXAMPLE 13

Synthesis of trans-ethyl 2,2-dimethyl-3-(2-chloro-2-(1,1,1,3,3,3-hexafluoro-2-propyloxy)-difluoromethyl)ethenylcyclopropanecarboxylate 20 cc of anhydrous THF and 480 mg of a suspension containing 50% of NaH in vaseline oil (10 mmoles) were loaded into a 3-neck flask equipped with a dropping funnel and magnetic stirrer. 1.68 g (10 mmoles) of 1,1,1,3,3,3-hexafluoro-2-propanol were added cautiously to the suspension, while keeping the temperature at 20° C.

After a few minutes 3.1 g (10 mmoles) of trans-ethyl 2,2-dimethyl-3-(1-acetoxy-2-chloro-3,3-difluoro)2-propenyl cyclopropanecarboxylate were dripped at room temperature. The mixture was stirred at room temperature over 2 hours. The reaction was stopped by means of 30 cc of a solution saturated with $NH_4Cl$; the mixture was extracted with ether, rinsed with a solution saturated with sodium bicarbonate and with brine, dehydrated and dried. After silica gel chromatography 3.6 g of product (86%) were obtained.

EXAMPLE 14

Synthesis of trans-ethyl 2,2-dimethyl-3-(2-chloro-2-isopropylthio-difluoromethyl)ethenyl-cyclopropanecarboxylate 20 cc of anhydrous THF and 480 mg of a suspension containing 50% of NaH in vaseline oil (10 mmoles) were loaded into a 3-neck flask equipped with dropping funnel and magnetic stirrer. 0.76 g (10 mmoles) of isopropanethiol were added cautiously to the suspension, while keeping the temperature at 20° C.

After a few minutes, 3.1 g (10 mmoles) of trans-ethyl 2,2-dimethyl-3-(1-acetoxy-2-chloro-3,3-difluoro)2-propenylcyclopropanecarboxylate were dripped at room temperature. The mixture was stirred at room temperature over 2 hours. The reaction was stopped by means of 30 cc of a solution saturated with $NH_4Cl$; the mixture was extracted with ether, rinsed with a solution saturated with sodium bicarbonate and with brine, dehydrated and dried. After silica gel chromatography, 2.8 g of product (86%) were obtained.

EXAMPLE 15

Synthesis of trans-ethyl 2,2-dimethyl-3-(2-fluoro-2-(2,2,2-trifluoroethoxy)-difluoromethyl)ethenyl)-cyclopropanecarboxylate 20 cc of anhydrous THF and 480 mg of a suspension containing 50% of NaH in vaseline oil (10 mmoles) were loaded into a 3-neck flask equipped with dropping funnel and magnetic stirrer. 1 g (10 mmoles) of 2,2,2-trifluoroethanol was added to the suspension cautiously, while keeping the temperature at 20° C.

After a few minutes the solution, when limpid, was cooled down to −30° C. and a solution of 2.95 g (10 mmoles) of trans-ethyl 2,2-dimethyl-3-(1-acetoxy-2-fluoro-3,3-difluoro)2-propenyl-cyclopropanecarboxylate was dripped into the cooled solution. After 15 minutes at −30° C. the reaction was stopped by means of 30 cc of a solution saturated with NH₄Cl; the mixture was extracted with ether, rinsed with a solution saturated with sodium bicarbonate and with brine, dehydrated and dried. After a quick silica gel chromatography, 2.9 g of product (1) (87%) were obtained.

N.M.R. (CDCl₃) δ: 1.05–1.3 (m. 9H); 1.55 (d. 1H); 2.2 (dd. 1H); 3.85–4.3 (m. 4H); 5.15 (dd. 1H).

EXAMPLE 16

Determination of the Insecticidal and Acaricidal Activity

A. Insecticidal activity against *Macrosiphum euphorbiae* (aphides). Small plants of potato grown in pots, were infested with adult females of aphis and, after a few hours, sprinkled with a water-acetone (acetone 10% by volume) suspension of the product being tested. 24 hours after the treatment, the percentage of the aphis mortality was determined, in comparison with that of aphides infesting small plants, only treated with an aqueous solution containing 10% of acetone.

B. Insecticidal activity against *Leptinotarsa decemlineata* (coleoptera).

Small plants of potato grown in pots were infested with coleopter larvae 4 days of age. Then the small plants were sprinkled with a water-acetone (acetone 10% by volume) dispersion containing the product being tested. The percentage of the larva mortality was evaluated 48 hours after the treatment, in comparison with that of larvae infesting small plants, only sprinkled with an aqueous solution of acetone at 10%.

C. Insecticidal activity against *Aedes aegypti* (Diptera).

Dipter larvae 4 days of age were brought into vessels containing 300 ml of an aqueous solution at 1% of acetone, containing the product being tested. After 48 hours the percentage of larva mortality was determined, in comparison with that of larvae brought into an aqueous solution that only contained acetone at 1%.

D. Acaricidal activity against *Tetranychus Urticae*

Adults

Small disks, obtained from bean leaves, were infested with adult acari and then sprinkled with a water-acetone (acetone 10% by volume) solution containing the product being tested. The mortality percentage was determined 24 hours after the treatment, in comparison with that of acari infesting small disks that had been only sprinkled with an aqueous solution containing 10% of acetone.

Eggs

Small disks, obtained from bean leaves, were infested with acarus eggs and then sprinkled with a water-acetone solution containing the product being tested. The percentage of unopened eggs was evaluated 7 days after the treatment, in comparison with that of eggs that had been only treated with water-acetone mixture.

By operating according to the above-described conditions, the compounds of the invention were tested in order to determine both the insecticidal and the acaricidal activity.

The insecticidal activity was evaluated according to the percentage of insect mortality at different doses of active compound, and was expressed according to the following scale of values:

| | |
|---|---|
| 5 = complete activity | mortality above 90% |
| 4 = high activity | mortality ranging from 80 to 90% |
| 3 = fairly good activity | mortality ranging from 60 to 79% |
| 2 = middling activity | mortality ranging from 40 to 59% |
| 1 = scanty activity | mortality ranging from 20 to 39% |
| 0 = negligible activity | mortality ranging from 0 to 19% |

The results of the test thus carried out are recorded in Table 1.

TABLE 1

| Dose Compound No. | Macrosiphum Euphorbiae (10) ppm | Aedes Aegypti (0.02 ppm) Activity | Tetranychus Urticae Adults 0.1%° | Tetranychus Urticae Eggs (0.1%°) |
|---|---|---|---|---|
| 1 | 5 | 5 | 5 | 5 |
| 3 | 5 | untested | untested | untested |
| 4 | 5 | untested | untested | untested |
| 5 | 5 | 5 | 3 | 4 |
| 6 | 5 | 5 | 2 | 4 |
| 9 | 5 | 5 | 5 | 5 |
| 11 | 5 | 5 | 5 | 5 |
| 14 | 5 | 5 | 4 | 3 |
| 15 | 5 | 5 | 2 | 2 |

What is claimed is:

1. Compounds having the formula $$R-Y-CF_2\overset{X}{C}=CH-\underset{\triangle}{\overset{CH_3\quad CH_3}{\diagup\diagdown}}-COOR_1 \quad (I)$$

wherein
R represents an alkyl, cycloalkyl, alkenyl or alkynyl group containing from 1 to 8 carbon atoms, optionally substituted with halogen atoms or R represents an aryl group, optionally substituted with halogen atoms; alkyl or alkoxyl radicals;
Y represents O or S;
X represents H, F, Cl, Br, —CH₃ or —CF₃;
R₁ represents a group having the formula:

[structure showing diphenyl ether/methane with substituents Q, A, X₁, X₂, CH—]

wherein X₁ is H or F; X₂ is H, —CN or —C≡CH; Q is O or CH₂; A is CH or N when X₁ is H, X₂ is CN and Q is O.

2. A compound according to claim 1, namely: trans-α-cyano-m-phenoxybenzyl 2,2-dimethyl-3-(2-chloro-2-methoxydifluoromethyl)vinylcyclopropanecarboxylate.

3. A compound according to claim 1, namely: 3-phenoxybenzyl 2,2-dimethyl-3-(2-chloro-2-(2,2,2-trifluoroethoxy)-difluoromethyl)-ethenyl-cyclopropanecarboxylate.

4. A compound according to claim 1, namely: α-cyano-3-phenoxybenzyl 2,2-dimethyl-3-(2-chloro-2-

(2,2,2-trifluoroethoxy)-difluoromethyl-ethenyl-cyclopropanecarboxylate.

5. A compound according to claim 1, namely: 3-phenoxy-4-fluorobenzyl 2,2-dimethyl-3-(2-chloro-2-(2,2,2-trifluoroethoxy-difluoromethyl-ethenyl-cyclopropanecarboxylate.

6. A compound according to claim 1, namely: α-cyano-3-phenoxy-4-fluorobenzyl 2,2-dimethyl-3-(2-chloro-2-(2,2,2-trifluoroethoxy)-difluoromethyl)-ethenyl-cyclopropanecarboxylate.

7. A compound according to claim 1, namely: α-cyano-3-phenoxybenzyl 2,2-dimethyl-3-(2-fluoro-2-(2,2,2-trifluoroethoxy)-difluoromethyl)-ethenyl-cyclopropanecarboxylate.

8. A compound according to claim 1, namely: α-cyano-3-phenoxybenzyl 2,2-dimethyl-3-(2-chloro-2-(2,2,3,3-tetrafluoropropoxy-difluoromethyl-ethenyl-cyclopropanecarboxylate.

9. A method of fighting infestations of noxious insects and acari consisting in distributing in the infestation area an effective amount of one or more compounds as claimed in claim 1, together with inert solid or liquid carriers.

10. Insecticide and acaricide compositions containing as active ingredient one or more compounds as claimed in claim 1, together with inert solid or liquid carriers.

* * * * *